（12） United States Patent
Holmes

(10) Patent No.: US 10,749,775 B2
(45) Date of Patent: Aug. 18, 2020

(54) SYSTEMS AND METHODS FOR RESPONSE CALIBRATION

(71) Applicant: Theranos, Inc., Palo Alto, CA (US)

(72) Inventor: Elizabeth A. Holmes, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 113 days.

(21) Appl. No.: 14/035,762

(22) Filed: Sep. 24, 2013

(65) Prior Publication Data

US 2014/0095189 A1    Apr. 3, 2014

Related U.S. Application Data

(63) Continuation-in-part of application No. PCT/US2012/057155, filed on Sep. 25, 2012, which
(Continued)

(51) Int. Cl.
*G16H 10/20*    (2018.01)
*H04L 12/26*    (2006.01)
(Continued)

(52) U.S. Cl.
CPC .......... *H04L 43/0811* (2013.01); *G06F 13/00* (2013.01); *G16H 10/20* (2018.01);
(Continued)

(58) Field of Classification Search
CPC .............................. G06Q 50/22; G06Q 50/24
See application file for complete search history.

(56) References Cited

U.S. PATENT DOCUMENTS

2004/0267562 A1* 12/2004 Fuhrer ............... G06F 19/366
    705/2
2006/0257402 A1* 11/2006 Chvatchko ........... A61K 38/177
    424/144.1
(Continued)

FOREIGN PATENT DOCUMENTS

EP    0828222 B1    3/2010
JP    2002222266 A    8/2002
(Continued)

OTHER PUBLICATIONS

Helton, K. L. (2007). Preconditioning saliva to measure small analytes in a microfluidic biosensor (Order No. 3293487). Available from ProQuest Dissertations and Theses Professional. (304810557). Retrieved from http://dialog.proquest.com/professional/docview/304810557?accountid=131444 (Year: 2007).*
(Continued)

*Primary Examiner* — Lena Najarian

(57) ABSTRACT

The disclosure provides methods, systems, and computer readable media for calibrating user responses to questions. The method may comprise presenting, with the aid of a computer system and an interactive display operatively coupled to the computer system, a query to a user. The query may relate to the user's dietary consumption, exercise, health condition or mental condition. The system may receive from the user a response to the query. The system may interpret a user's response to a query based on a set of reference information. The set of reference information may comprise a pictorial depiction of portion size of the dietary consumption, exertion level of the exercise, existing state of the health condition or existing state of the mental condition.

20 Claims, 15 Drawing Sheets

Related U.S. Application Data is a continuation of application No. 13/244,836, filed on Sep. 26, 2011, now Pat. No. 8,392,585, and a continuation of application No. 13/244,946, filed on Sep. 26, 2011, now Pat. No. 8,380,541, and a continuation of application No. 13/244,947, filed on Sep. 26, 2011, now Pat. No. 8,435,738, and a continuation-in-part of application No. PCT/US2011/053189, filed on Sep. 25, 2011, and a continuation-in-part of application No. PCT/US2011/053188, filed on Sep. 25, 2011.

(60) Provisional application No. 61/705,552, filed on Sep. 25, 2012.

(51) Int. Cl.

| | | |
|---|---|---|
| *H04W 76/18* | (2018.01) | |
| *H04L 12/24* | (2006.01) | |
| *H04L 12/707* | (2013.01) | |
| *H04L 12/703* | (2013.01) | |
| *H04L 12/911* | (2013.01) | |
| *G06F 13/00* | (2006.01) | |
| *H04L 29/08* | (2006.01) | |

(52) U.S. Cl.
CPC .... *H04L 29/08234* (2013.01); *H04L 41/0654* (2013.01); *H04L 43/10* (2013.01); *H04L 45/22* (2013.01); *H04L 45/28* (2013.01); *H04L 47/728* (2013.01); *H04L 47/746* (2013.01); *H04L 67/1023* (2013.01); *H04W 76/18* (2018.02)

(56) References Cited

U.S. PATENT DOCUMENTS

| | | | |
|---|---|---|---|
| 2006/0287883 A1* | 12/2006 | Turgiss | G06F 19/3418 705/2 |
| 2008/0071794 A1* | 3/2008 | Barnard | 707/10 |
| 2011/0143947 A1 | 6/2011 | Chamberlin et al. | |
| 2012/0059664 A1 | 3/2012 | Georgiev et al. | |
| 2012/0179665 A1* | 7/2012 | Baarman et al. | 707/709 |
| 2014/0073043 A1 | 3/2014 | Holmes | |

FOREIGN PATENT DOCUMENTS

| | | |
|---|---|---|
| JP | 2006155010 A | 6/2006 |
| JP | 2007334653 A | 12/2007 |
| JP | 2011129034 A | 6/2011 |
| JP | 2012112855 A | 6/2012 |
| WO | 2013043203 A | 3/2013 |

OTHER PUBLICATIONS

International Search Report and Written Opinion dated Jan. 16, 2014 for Application No. PCT/US2013/061485.

\* cited by examiner

300

|  | Apple | Orange |
|---|---|---|
| Small | 1 | 1 |
| Medium | 3 | 5 |
| Large | 5 | 8 |

Enter details for Ham, Sliced

How big is 1 serving of sliced ham?

| Picture 1 | Picture 2 | Picture 3 |

◀ Back    Add to Food Diary

FIG. 8

Enter a few details for Bike Riding:

Which image corresponds with Intensity: moderate?

| Picture 1 | Picture 2 | Picture 3 |

Today's Survey

Which image corresponds with Well-being: 6?

| Picture 1 | Picture 2 | Picture 3 |

Next

FIG. 13

SYSTEMS AND METHODS FOR RESPONSE CALIBRATION

CROSS REFERENCE

This application claims the benefit of U.S. Provisional Application No. 61/705,552 filed Sep. 25, 2012, which is incorporated by reference herein in its entirety for all purposes.

BACKGROUND

A questionnaire is a series of questions or other prompts for the purpose of gathering information from a respondent. A questionnaire may be a research instrument designed for statistical analysis of user responses.

A questionnaire may be presented to a user with the aid of a computer system having a graphical user interface (GUI). A GUI is a type of user interface that allows users to interact with electronic devices through images and text commands. GUIs can be used, for example, in computers, hand-held devices such as MP3 players, portable media players, mobile phones, gaming devices, household appliances and office equipment. In some cases, a GUI represents the information and actions available to a user through graphical icons and other visual indicators, such as secondary notation, as opposed to text-based interfaces, typed command labels, voice commands and responses, brail interface or text navigation.

There are various issues and limitations associated with questionnaire systems and methods currently available. For instance, a questionnaire may present a user with the following question: "How large was your lunch?" The questionnaire may present the user with various response options to select from, such as "small", "medium" and "large." The user's selection of one of these options typically does not provide an individual providing the questionnaire the ability to interpret the user's response.

SUMMARY

Recognized herein is the need for improved questionnaires and systems for providing the questionnaires. For instance, what is needed is a system to provide a user a questionnaire (e.g., guided questionnaire) while readily assessing user response to questions posed by the questionnaire.

Typically, it may be difficult to assess a user's response to questions in a questionnaire. For instance, if a user is presented with the question "How large was your lunch?," if the user selects "medium", the individual providing the questionnaire has no way of determining what the user meant by "medium." To the user, "medium" may mean, for example, a half plate, a full plate, or a plate and a half of food. In another example, a user may be incapable of effectively assessing quantity. For instance, a user's selection of "medium" in one context or point in time might be different from the user's selection of "medium" in another context or point in time. Accordingly, provided herein are improved questionnaires, systems for providing questionnaires, and related methods and computer readable media.

In one embodiment, a computer-implemented method for calibrating user responses to questions relating to dietary consumption, exercise, health condition, or mental condition is provided, the method including: (a) presenting, with the aid of a computer system and an interactive display operatively coupled to the computer system, a query to a user, said query relating to said user's dietary consumption, exercise, health condition or mental condition; (b) receiving, with the aid of said computer system and interactive display, a response to said query from said user; and (c) interpreting, with the aid of a computer processor, said response based on a set of reference information, wherein said set of reference information comprises a pictorial depiction of portion size of said dietary consumption, exertion level of said exercise, existing state of said health condition or existing state of said mental condition. The method may include, subsequent to step (c), monitoring the health of said user.

In another embodiment, a computer-implemented method for calibrating user responses to questions relating to dietary consumption, exercise, health condition, or mental condition is provided, the method including: (a) presenting, with the aid of a computer system and an interactive display operatively coupled to the computer system, a query to a user, the query relating to the user's dietary consumption, exercise, health condition or mental condition; (b) receiving, with the aid of the computer system and interactive display, a response to the query from the user; and (c) interpreting, with the aid of the computer system, the response based on a calibration matrix having a set of reference information, the reference information generated with the aid of a pictorial depiction of portion size of the dietary consumption, exertion level of the exercise, existing state of the health condition or existing state of the mental condition. The method may include, subsequent to step (c), monitoring the health of said user.

In another embodiment, provided herein is a computer readable medium comprising machine-executable code implementing a method for calibrating user responses to questions relating to dietary consumption, exercise, health condition, or mental condition, including: (a) presenting, with the aid of a computer system and an interactive display operatively coupled to the computer system, a query to a user, the query relating to the user's dietary consumption, exercise, health condition or mental condition; (b) receiving, with the aid of said computer system and interactive display, a response to said query from said user; and (c) interpreting, with the aid of said computer system, said response based on a set of reference information, wherein said set of reference information comprises a pictorial depiction of portion size of said dietary consumption, exertion level of said exercise, existing state of said health condition, or existing state of said mental condition. The method for calibrating user responses to questions relating to dietary consumption, exercise, health condition, or mental condition may include, subsequent to step (c), monitoring the health of said user.

In another embodiment, a system for calibrating user responses to questions relating to dietary consumption, exercise, health condition, or mental condition, is provided, the system including: an interactive display configured to present machine-generated graphical items to a user; and a computer system operatively coupled to said interactive display, said computer system having a memory location comprising machine-executable code implementing, with the aid of a processor of said computer system, a method comprising: (a) presenting, with the aid of said computer system and interactive display, a query to a user, said query relating to said user's dietary consumption, exercise, health condition or mental condition; (b) receiving, with the aid of said computer system and interactive display, a response to said query from said user; and (c) interpreting, with the aid of said computer system, said response based on a set of reference information, wherein said set of reference information comprises a pictorial depiction of portion size of said dietary consumption, exertion level of said exercise, existing state of said health condition, or existing state of said mental condition. The method may include, subsequent to step (c), monitoring the health of said user.

In some embodiments, in a method, system, or computer readable medium described above or elsewhere herein involving reference information, the reference information is obtained by providing to a user a choice of at least two pictorial elements, wherein the pictorial elements depict portion size, exertion level, existing state of a health condition, or existing state of a mental condition.

In some embodiments, in a method, system, or computer readable medium described above or elsewhere herein involving reference information, the reference information is utilized to yield a calibration matrix to calibrate a user's response to a query relating to the user's dietary consumption, exercise, health condition or mental condition.

In some embodiments, in a method, system, or computer readable medium described above or elsewhere herein involving an interactive display, the interactive display is a capacitive touch or resistive touch display.

In some embodiments, in a method, system, or computer readable medium described above or elsewhere herein involving reference information, the reference information is obtained or presented prior to a query to a user relating to the user's dietary consumption, exercise, health condition or mental condition In some embodiments, in a method, system, or computer readable medium described above or elsewhere herein involving reference information, the reference information is obtained or presented subsequent to a query to a user relating to the user's dietary consumption, exercise, health condition or mental condition.

In some embodiments, in a method, system, or computer readable medium described above or elsewhere herein involving reference information, the reference information is obtained or presented concurrently with a query to a user relating to the user's dietary consumption, exercise, health condition or mental condition.

In some embodiments, in a method, system, or computer readable medium described above or elsewhere herein involving a user's response to a query relating to the user's dietary consumption, exercise, health condition or mental condition, the response is interpreted with the aid of a calibration matrix residing on a memory location of a computer system.

In some embodiments, in a method, system, or computer readable medium described above or elsewhere herein involving a user's response to a query relating to the user's dietary consumption, exercise, health condition or mental condition, the query is presented to the user with the aid of a graphical user interface (GUI) on an interactive display.

In some embodiments, in a method, system, or computer readable medium described above or elsewhere herein involving a GUI, the GUI includes a customizable menu screen containing a choice of at least one, two, three, or four of the following applications: (a) a dietary consumption component, including information concerning a user's diet and an interface for entering food, drink or other related information; (b) an exertion level component having information related to a user's activity habits or schedule, and an interface for entering user-specific activity information, exercise or other user-specific activity-related information; (c) a health condition component having information concerning a user's health, and an interface for responding to queries or entering information related to the user's health condition; (d) a mental condition component having information concerning a user's mental condition, and an interface for responding to queries or entering information related to the user's mental condition; and (e) a calibration questionnaire component, wherein a user is presented with at least one choice of pictorial elements relating to dietary consumption, exercise, health condition or mental condition, and the user's choice of a pictorial element is used to build a calibration matrix to interpret the user's perception of portion size of dietary consumption, exertion level of exercise, existing state of health condition or existing state of mental condition.

In some embodiments, in a method, system, or computer readable medium described above or elsewhere herein involving a calibration matrix, the calibration matrix resides on a memory location of a computer system.

In some embodiments, in a method, system, or computer readable medium described above or elsewhere herein involving a user's response to a question relating to dietary consumption, exercise, health condition, or mental condition, the response is interpreted using an internal calibration matrix of the user's perception of portion size of said dietary consumption, exertion level of said exercise, existing state of said health condition or existing state of said mental condition.

In some embodiments, in a method, system, or computer readable medium described above or elsewhere herein involving an internal calibration matrix, the internal calibration matrix is stored on a memory location of a computer system.

In some embodiments, in a method, system, or computer readable medium described above or elsewhere herein involving a customizable menu screen, the customizable menu screen contains a choice of at least two of said applications.

In some embodiments, in a method, system, or computer readable medium described above or elsewhere herein involving a system, the system is a point of service system configured to perform one or more assays on a sample.

In some embodiments, in a method, system, or computer readable medium described above or elsewhere herein involving a point of service system, the point of service system is configured to perform one, two, three or more assays on a sample.

In one embodiment described herein, a computer-implemented method is provided for calibrating user responses to questions relating to dietary consumption, exercise, health condition, or mental condition. The method comprises (a) presenting, with the aid of a computer system and an interactive display operatively coupled to the computer system, a query to a user, said query relating to said user's dietary consumption, exercise, health condition and/or mental condition; (b) receiving, with the aid of said computer system and interactive display, a response to said query from said user; and (c) interpreting, with the aid of a computer processor, said response based on a set of reference information, wherein said set of reference information comprises pictorial depictions displayed to the user showing portion size of said dietary consumption, exertion level of said exercise, existing state of health condition and/or existing state of mental condition, wherein the set of reference information is generated by a) the user selecting pictorial depictions that best matches their qualitative descriptions and b) mapping quantitative information associated user selected pictorial depictions to quantify user qualitative descriptions.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In the drawings,

FIG. 8 shows an illustrative example of a screenshot of a reference question for interpreting the information provided by the user in FIG. 7;

FIG. 13 shows an illustrative example of a screenshot of a reference question for interpreting the information provided by the user in FIG. 12.

DETAILED DESCRIPTION

Figure 1:
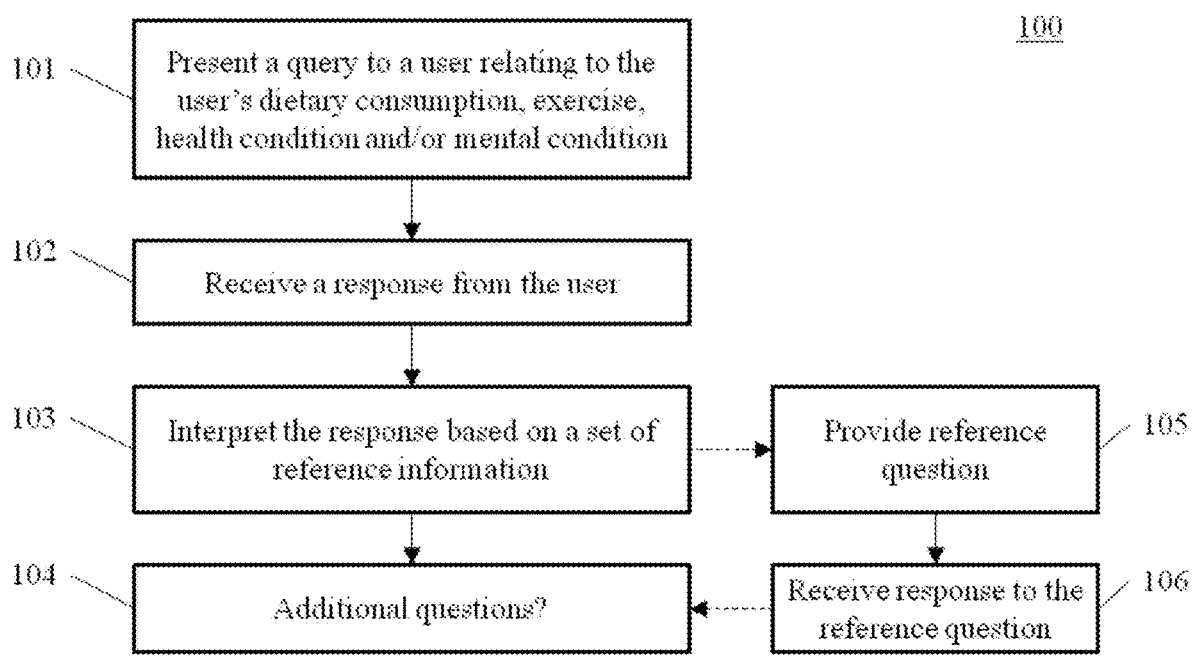
FIG. 1 shows an illustrative example of a method for providing a questionnaire to a user.

While various embodiments have been shown and described herein, it will be obvious to those skilled in the art that such embodiments are provided by way of example only. Numerous variations, changes, and substitutions may occur to those skilled in the art without departing from the systems and methods provided herein.

The term "health condition," as used herein, refers to physiological condition and/or mental condition. Mental condition may include the mood or mental state (e.g., depression) of a subject.

The term "point of service system," as used herein, refers to a system that is capable of providing a service (e.g. testing, monitoring, treatment, diagnosis, guidance, sample collection, ID verification, medical services, non-medical services, etc.) at or near the site or location of the subject. In some situations, a point of service system provides a service at a predetermined location, such as a subject's home or work, a grocery store, or a drug store. A point of service system can include one or more point of service devices.

The term "subject," as used herein, refers to an individual whose health is being monitored or that is in need of treatment or monitoring. In some instances, a subject is an individual receiving or in need of treatment and who is under the care of, or being acted upon by, a point of service system. A subject may include a patient. In some cases, the subject is a human patient. A subject can be a user of a point of service device (or system), or a user of a computer system associated with the point of service device. In some cases the terms "subject" and "user" can be used interchangeably.

The term "cloud computing" (or "cloud"), as used herein, refers to a system in which shared resources, software and information are provided to computers and other devices as a utility over a network, such as the Internet. A cloud can include a distributed network. Shared resources may include various computer systems, such as servers, that may be provided in a distributed fashion but are operatively coupled to one another.

The term "dietary consumption," as used herein, refers to a substance (solid, liquid, or semi-solid) that is ingested (or consumed) by a user, or which the user plans on ingesting. Analysis of dietary consumption in some cases can include information relating to a drug (or medication) consumed, supplement (e.g., vitamin) consumed or a metabolite thereof, cholesterol consumed, fat consumed, protein consumed, fiber consumed, carbohydrate consumed, salt consumed, and/or liquid consumed. Analysis of dietary consumption can be aided with bar-coded information or downloadable information on the composition of a food product, or photograph(s) of the food and/or liquid consumed, such as a meal.

The term "exercise," as used herein, refers to an activity of a user that helps enhance or maintain the physical fitness of that user. A user's exercise can include sports activities, workout routines (e.g., jogging, running), physical labor, and other training activities.

The term "health condition," as used herein, refers to the physical condition of a subject. Health condition can include the level of functional and/or metabolic efficiency of the subject.

The term "mental condition," as used herein, refers to the condition of the mind of a subject, including, without limitation, psychological state and/or emotion of the subject.

In some embodiments, provided herein are systems and methods for enabling a ready assessment of user responses to questionnaire questions. Methods provided herein, which can be implemented by systems provided herein, enable the calibration of user responses to questions posed during a questionnaire (or survey) to improve the accuracy of the interpretation of user responses to the questions. In some situations, this permits the system to determine what the user means by a particular response, such as quantity or quality.

In some embodiments, systems are provided to enable a user to collect physiological data measuring changes in various physiological parameters, such as, for example, blood pressure, pulse rate, oxygen saturation, electrophysiology, iris dilation, and skin conductivity in response to questions. Such physiological data can supplement questionnaire questions collected from the user. Such information can be used to monitor the health of the user, or in some cases to diagnose and/or treat the user.

Questionnaire Methods

In some embodiments, provided herein are methods for calibrating user responses to one or more questions. The questionnaire includes one or more questions that are interpreted with the aid of a user's response to one or more reference questions. In some situations, the reference questions are used to build a calibration matrix, which is subsequently used to interpret user response to questions provided in the questionnaire. In some cases, the questionnaire includes questions relating to a user's dietary consumption, exercise, health condition and/or mental condition.

In some embodiments, a computer-implemented method for calibrating user responses to questions relating to dietary consumption, exercise, health condition, or mental condition comprises presenting a query to a user (or subject) with the aid of a computer system and an interactive display operatively coupled to the computer system. The query may relate to the user's dietary consumption, exercise, health condition and/or mental condition, or in some cases the query can relate to other factors related to the user, such as the subject's sleep (e.g., sleep pattern), mood, exercise history, stress levels, health history, hormone status, and/or menstrual cycle. Next, with the aid of the computer system and interactive display, a response to the query is received from the user. A processor is then used to interpret the response based on a set of reference information. In some embodiments, the set of reference information comprises a representation of portion size of the dietary consumption, exertion level of the exercise, existing state of health condition and/or existing state of mental condition. The representation can be pictorial, audible, or a combination thereof, such as video. In some cases, the set of reference information comprises a pictorial depiction of portion size of the dietary consumption, exertion level of the exercise, existing state of health condition and/or existing state of mental condition.

In some cases, the reference information is obtained by providing to the user a choice of at least 2, or 3, or 4, or 5, or 6, or 7, or 8, or 9, or 10, or 15, or 20, or 30, or 40, or 50, or 100 pictorial elements. The pictorial elements may depict the portion size, the exertion level, the existing state of the health condition, and/or the existing state of the mental condition.

In some embodiments, the reference information is obtained prior to the query. That is, a device or system implementing the query presents a reference question to the user prior to the actual query. In other embodiments, the reference information is obtained subsequent to the query. In such cases, the device or system implementing the query presents the reference question to the user after the actual query. In other embodiments, the reference information is obtained concurrently with the query. In such cases, the device or system implementing the query presents the user with the actual query and the reference question at the same time (e.g., in the same page).

In some embodiments, a computer-implemented method for calibrating user responses to questions relating to dietary consumption, exercise, health condition, or mental condition, comprises presenting, with the aid of a computer system and an interactive display operatively coupled to the computer system, a query to a user, the query relating to the user's dietary consumption, exercise, health condition and/or mental condition. Next, with the aid of the computer system and interactive display, a response to the query is received from the user. Next, with the aid of the computer system, the response is interpreted based on a calibration matrix having a set of reference information. The reference information may be generated with the aid of a pictorial depiction of portion size of the dietary consumption, exertion level of the exercise, existing state of health condition and/or existing state of mental condition.

FIG. 1 shows a method 100 for providing a questionnaire to a user provided herein. The questionnaire can be implemented with the aid of systems and devices provided herein. A system or device includes one or more processors for executing machine-readable code implementing the method 100. The machine readable code is stored in a memory location of the system or device. In some cases, the machine readable code is stored in remote system and, in some situations, executed in the remote system.

In a first step 101, a system implementing the questionnaire presents a user with a query having one or more questions (e.g., "How are you feeling today?"). The questions can be presented to the user with the aid of graphical, textual, audio, and/or video elements, such as a video of an actor or animation asking the user a question. These elements can be provided to the user with the aid of an interactive display of a system or device implementing the method 100. Next, in a second step 102, the user inputs a response into the system implementing the method 100 (e.g., "I am feeling moderately well"). The user can input the response using an interactive display or other input device of the system, such as a touch screen (e.g., capacitive touch screen, resistive touch screen), voice activation and/or gestures. Next, in a third step 103, the system interprets the response based on one or more reference information. In some cases, the system determines what the user meant by the user's response in the second step 102. In an example, the system interprets what the user means by "moderately well" in the context of well-being. Next, in a fourth step 104, the system determines whether there are additional questions to present to the user in the questionnaire. Steps 101-103 can then be repeated as necessary to present additional questions to the user.

In some embodiments, interpreting the user's response includes providing the user a reference question and receiving a response from the user to the reference question. With reference to FIG. 1, during the third step 103, the system interprets the user's response using one or more responses received from the user to reference questions posed to the user. In step 105, the user is presented with a reference question (e.g., "Which picture most closely approximates the mood 'moderately well'?"). Next, in step 106, the user selects a picture from the options. In some embodiments, steps 105 and 106 are repeated, such as to gain an assessment of user responses to various types of questions relating to the user's dietary consumption, exercise, health condition and/or mental condition, or to collect additional responses to interpret the user's response 103. The system then uses the user's response to the reference question to interpret the user's response 103.

The reference (or calibration) question can be used to interpret a user's response. In some embodiments, the reference information can include a pictorial depiction of portion size of dietary consumption, exertion level of exercise, existing state of health condition and/or existing state of mental condition. The reference question can be presented to the user at least 1, 2, 3, 4, 5, 6, 7, 8 9, 10, 20, 30, 40, 50, 100, or more times per questionnaire session ("session"), or every other session, or once per a group of sessions, or periodically, such at least every 1, 2, 3, 4, 5, 6, 7, 8, 9, 10, 20, 30, or more days.

Figure 2A:
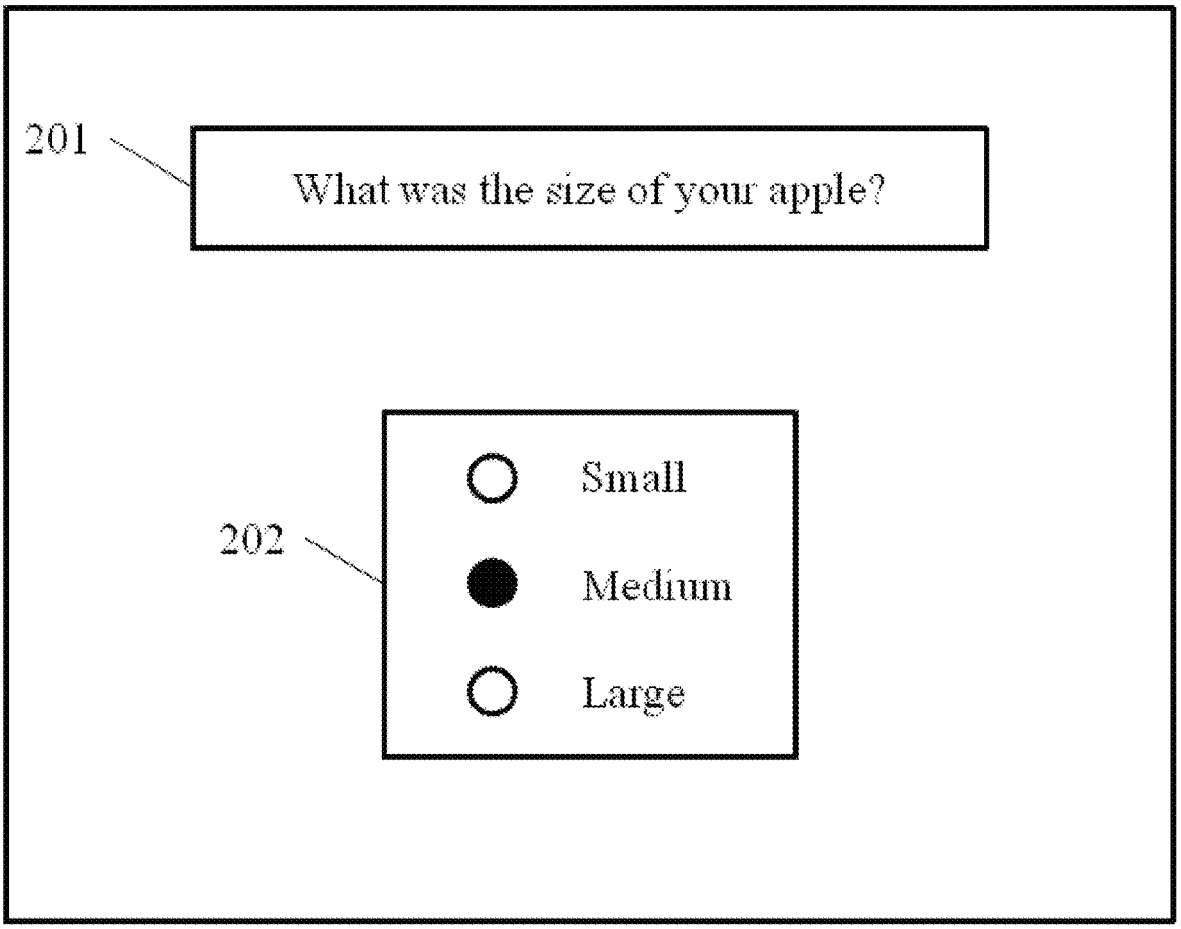
FIGS. 2A and 2B show an illustrative example of a method for presenting a questionnaire to a user.
Figure 2B:
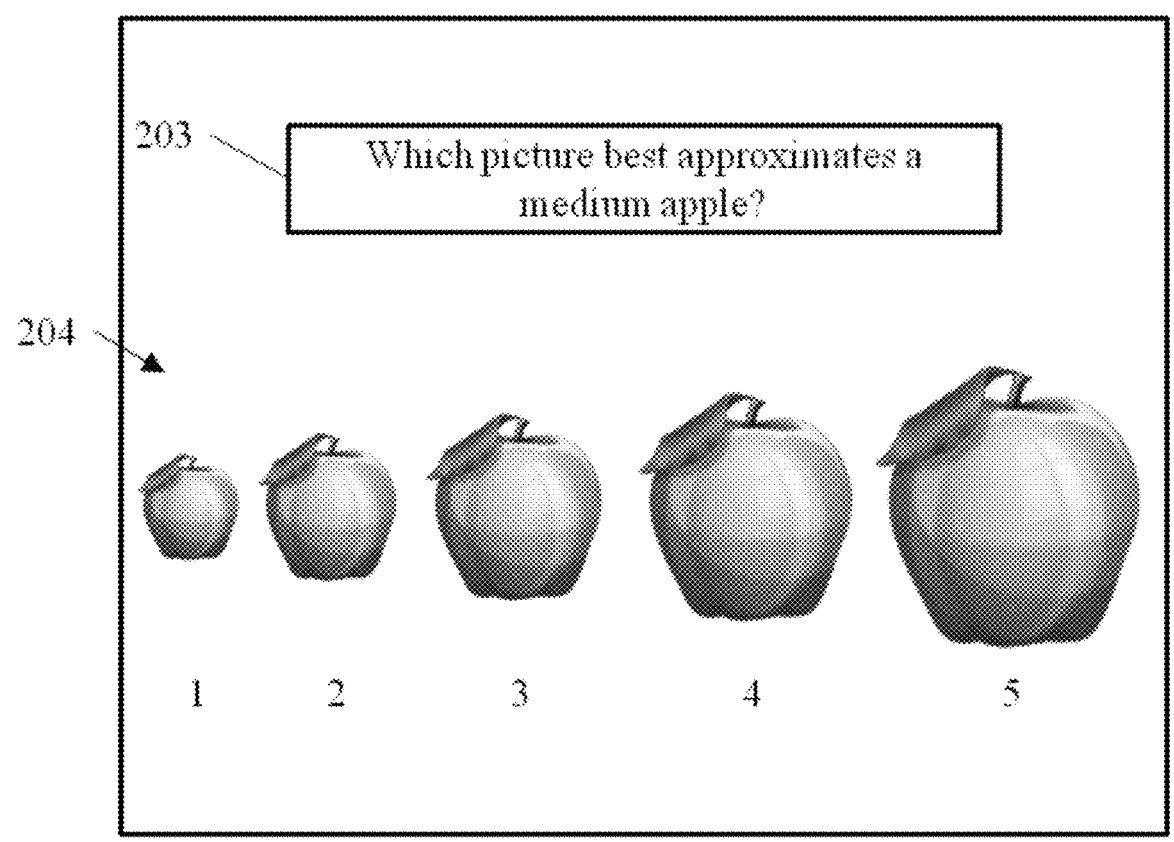

FIGS. 2A and 2B show an illustrative example of a method for presenting a questionnaire to a user. In FIG. 2A, in a first screen, the user is presented with a question 201, namely "What was the size of your apple?" The user is presented with three options 202, namely "Small", "Medium" and "Large." The user selects "Medium." With reference to FIG. 2B, in a second screen, the system presents the user with a reference (or calibration) question 203, namely "Which picture best approximates a medium apple?" In some embodiments, the calibration question gauges the user's perception of quantitative or qualitative factors, such as portion size. The system also presents the user with three images of apples, at least one of which may correspond with the user's definition of the term "Medium." Alternatively, the system can first present the user with the reference question 203, and subsequently present the user with the question 201. As another alternatively, the reference question 203 and question 201 can be presented simultaneously (e.g., on the same screen). The user's selection of one of the images 204 enables the system to interpret the user's response to the question 201. In some embodiments, this can be used to normalize other responses, such as other responses related to the user's diet. The number below each of the images 204 is a numeric representation of the image 204, which may be hidden from the user. For instance, the number "3" represents the apple in the middle.

Although FIG. 2B provide five images to calibrate the size of an apple, the calibration question can present the user with any number of apples, such as at least 1, 2, 3, 4, 5, or 6, or 7, or 8, or 9, or 10, 20, 30, 40, or more apples of varying sizes. FIGS. 2A and 2B are described in the context of apples, but FIGS. 2A and 2B can be applied to other contexts, such as to other foods or consumable substances, exercise, health condition and mental conditions.

In some embodiments, an image of an object may be presented on a screen, wherein the image on the screen has the same height, length, and/or width as a dimension of the actual object which is the presented as an image (e.g. if the real height of an apple is 8 cm, an image of that apple on a screen also has a height of 8 cm). In some embodiments, an image of an object may be presented on a screen with an image of a reference object of a standard size (e.g. a tennis ball, a United States quarter, a ruler) at the same scale. By presenting an image of an object on a screen with an image of a reference object of a standard size at the same scale, a user may readily associate a certain size of an image on a screen with the dimensions of the actual object corresponding to the image on the screen. This may be useful, for example, if the image of an object on a screen has a different height, length, and/or width than a dimension of the corresponding actual object (e.g. if the real height of an object is 10 cm, but an image of that object on a screen only has a height of 2 cm).

In some embodiments, a user is presented with a reference question once. The user's response to the reference questions is used in subsequent questionnaire questions. As such, a questionnaire question may not be necessarily followed by a calibration questions in each instance.

In some situations, the system makes use of responses to calibration questions for interpreting user responses to subsequent questionnaire questions. The system can ask the user calibration questions at predetermined intervals or at pseudo-random points during the questionnaire to assess the accuracy of the calibration responses.

The system can present a user with a reference question within a particular category (e.g., dietary consumption, exercise, health condition or mental condition) and receive a response from the user. This provides category-specific calibration. For subsequent questionnaire questions within the same category, the system uses the category-specific calibration to interpret user responses.

Calibration questions and/or options for a user (or subject) to choose from within a calibration question can be fixed based on the user's responses to prior calibration or questionnaire questions, or may vary based on the user's responses. In some cases, response choices presented to the user for a calibration question is a function of the user's response to a questionnaire question (see, e.g., Example 3).

In some situations, calibration questions are used to assess the internal consistency of the user. This can permit the system to flag instances in which the user inputs a response to a questionnaire question that is inconsistent with the user's responses to other questions. The system may calibrate flagged response more frequently. In other situations, the calibration question may preclude the need for selecting an image that corresponds to a response to a question. For example, with reference to FIGS. 2A and 2B, once the system has been calibrated, the calibration of FIG. 2B can be precluded and the system uses a prior response to a calibration question to determine what the user means by "Medium."

In some situations, the system builds and/or updates a calibration matrix having responses to calibration questions. The calibration matrix can include columns having calibration items, such as food items or activity level, and rows for quantity or degree of exertion, to name a few examples. Pictorial responses to questions (see, e.g., FIG. 2B) can be represented by numbers. For example, a small apple and medium apple can be represented by the numbers 1 and 3, respectively. The system can include a plurality of calibration matrixes for different types of questions, such as questions relating to dietary consumption, exercise, health condition and mental condition. A calibration matrix can be stored on a memory location of the system.

In some embodiments, a calibration matrix is located in a memory location of the system, such as a hard drive or data storage unit (e.g., database) of the system. The calibration matrix can thus be an internal calibration matrix. In other embodiments, the calibration matrix is an external calibration matrix that is located in a memory location of a remote computer system, which can be accessed by the system using a network. In an example, the calibration matrix is stored in the cloud and accessed by the system using wired or wireless network connectivity.

Figure 3:
FIG. 3 shows an illustrative example of a calibration matrix.

FIG. 3 shows an example of a calibration matrix 300 provided herein. The matrix includes columns and rows orthogonal to the columns, and cells at the intersections of columns and rows. The matrix 300 is for the category dietary consumption, which can relate to food items ingested by a user. The rows have values that correspond to potential sizes of food items, namely "Small," "Medium," and "Large." The columns have numeric representations of images selected by the user that correspond to the sizes. For instance, the cell at row "Small" for "Apple" has the number 1, which corresponds to the left-most image in FIG. 2B, and the cell at row "Medium" has the number 3, which corresponds to the middle image in FIG. 2B.

In some situations, the system provides the user direct comparisons to objects of given sizes, which can be used to supplement calibration data. In an example, the system asks the user to select the larger (or smaller) of two items.

A plurality of matrixes can be used to calibrate user responses to questions in various categories. A calibration matrix can be used to calibrate user responses to questionnaire questions relating to the user's mental condition (e.g., mood), exercise (e.g., level of activity) and/or health condition (e.g., sick). Calibration matrixes are not limited to the categories provided herein; calibration matrixes for other categories may be provided.

Questionnaires (or surveys) described herein can be implemented on any computer system having one or more processors, such as central processing units (CPUs). In some cases, a questionnaire is performed by a point of service device (see below) that, in some cases, is configured to processes a sample of a subject. In other cases, a questionnaire is performed by a computer system that may not be a point of service device, but can be in communication with the point of service device, such as through a network.

Systems

In some embodiments, provided herein are systems for implementing questionnaires (or surveys). A system can be a point of service system (or device). In some embodiments, a system for calibrating user responses to questions relating to dietary consumption, exercise, health condition, or mental condition includes an interactive display and a computer system operatively coupled to the interactive display. For example, the interactive display can be in communication with the computer system with the aid of a bus of the computer system, or a network. The interactive display is configured to present machine-generated graphical items to a user. The computer system includes a memory location comprising machine-executable code implementing, with the aid of a processor of the computer system, methods provided herein.

In an example, the memory location comprises machine-executable code implementing a method comprising presenting, with the aid of the computer system and interactive display, a query to a user, the query relating to the user's dietary consumption, exercise, health condition and/or mental condition. Next, with the aid of the computer system and interactive display, a response to the query is received from the user. With the aid of the computer system, the response is interpreted based on a set of reference information. The set of reference information comprises a pictorial depiction of portion size of the dietary consumption, exertion level of the exercise, existing state of health condition, and/or existing state of mental condition.

The interactive display can be a capacitive touch or resistive touch display. The display can have other functionality, such as the capability to collect biometric information from the user. For instance, the display can be used to measure the user's body-fat percentage with the aid of two-point touch through one or both hands of the user (e.g., the user places two fingers on the display). The display can also have chemical or electrical sensors to sense factors specific to the user (or subject) that may help identify the state or health condition of the subject.

In some embodiments, a point of service device can include a display having a user interface (UI). In some situations, the user interface is provided to a user through a graphical user interface (GUI) that may enable a subject to interact with device. The display can thus be an interactive display. Examples of displays and/or user interfaces include a touch screen, video display, LCD screen, CRT screen, plasma screen, light sources (e.g., LEDs, OLEDs), IR LED based surfaces spanning around or across devices, modules or other components, pixelsense based surface, infrared cameras or other capture technology based surfaces, projector, projected screen, holograms, keys, mouse, button, knobs, sliding mechanisms, joystick, audio components, voice activation, speakers, microphones, a camera (e.g., 2D, 3D cameras), multiple cameras (e.g., may be useful for capturing gestures and motions), glasses/contact lenses with screens built-in, video capture, haptic interface, temperature sensor, body sensors, body mass index sensors, motion sensors, and/or pressure sensors. Any description herein of a display and/or user interface may apply to any type of display and/or user interface.

A display may provide information to a user of the device (e.g., point of service device). A user interface may provide information to and/or receive information from the operator (or user). In some embodiments, such information includes visual information, audio information, sensory information, thermal information, pressure information, motion information, or any other type of information. Sound, video, and color coded information (such as red LED's indicating a module is in use) may be used to provide feedback to users using a point of service system or information system, or interfacing with a system through touch or otherwise. In some embodiments, a user interface or other sensor of the device detects if someone is approaching the device, and causes the device to "wake up" (i.e. become activated). The user interface or other sensor can also be used to put the system to "sleep" if no users are detected.

In some cases, a graphical user interface (GUI) is presented on an interactive screen containing a choice of at least one of the following applications: (a) a dietary consumption component, including information concerning the user's diet and an interface for entering food, drink or other related information; (b) an exertion level component having information related to the user's activity habits or schedule, and an interface for entering user-specific activity information, exercise or other user-specific activity-related information; (c) a health condition component having information concerning the user's health, and an interface for responding to queries and/or entering information related to the user's health condition; (d) a mental condition component having information concerning the user's mental condition, and an interface for responding to queries and/or entering information related to the user's mental condition; and (e) a calibration questionnaire component, wherein the user is presented with at least one choice of pictorial elements (including text, video and/or sound) relating to dietary consumption, exercise, health condition and/or mental condition, and the user's choice of a pictorial element is used to build a calibration matrix to interpret the user's perception of portion size of the dietary consumption, exertion level of the exercise, existing state of health condition, or existing state of mental condition. In some situations, the GUI comprises a customizable menu screen, which can permit a user or other individual (e.g., a health care provider, such as a doctor) to customize the menu screen.

Point of service systems (or devices) provided herein can be as described in U.S. patent application Ser. No. 13/244,947 to Holmes et al. and PCT application Ser. No. PCT/US2012/057155 entitled ("SYSTEMS AND METHODS FOR MULTI-ANALYSIS") filed Sep. 25, 2012, which are both fully entirely incorporated herein by reference for all purposes. A point of service system may perform one or more, 2 or more, 3 or more, 4 or more, 5 or more, 10 or more, 20 or more, 30 or more, 40 or more, 50 or more, or 100 or more assays on a sample. In some cases, a point of service system can perform sample processing, subsequent data processing and, in some cases, data analysis.

In other cases, a point of service system can perform sample processing and transmit pre-processed data to a remote system for data processing and, in some cases, analysis.

Figure 4A:
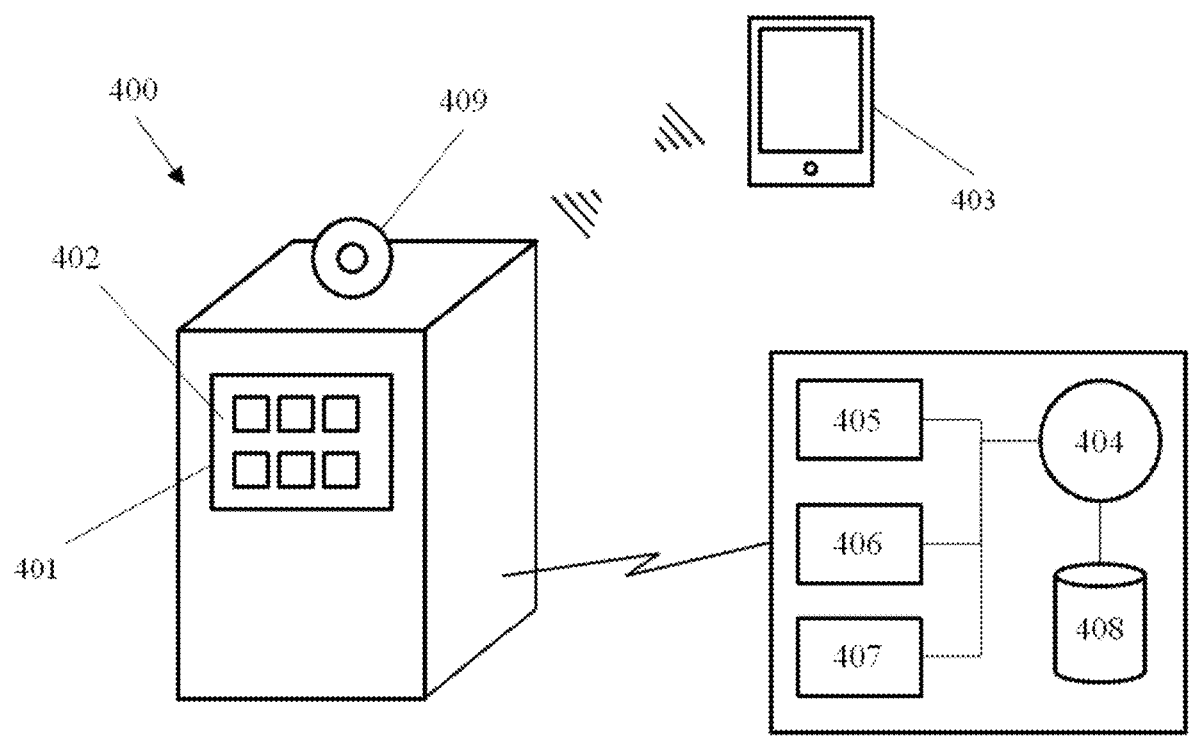
FIGS. 4A and 4B show an illustrative example of a system having a point of service device in communication with other devices.

FIG. 4A illustrates an example of point of service system (or device) 400 having a display 401. The display is configured to provide a user interface 402, such as a graphical user interface (GUI), to a subject. The display 401 can be a touch display, such as a resistive-touch or capacitive-touch display. The point of service system 400 is configured to communicate with a remote device 403, such as, for example, a personal computer, Smart phone (e.g., Apple® iPhone®, Android-enabled telephone), tablet (e.g., Apple® iPad®), or server. The point of service system 400 has a central processing unit (CPU) 404, memory 405, communications module (or interface) 406, hard drive 407 and data repository 408. The memory 405, communications module 406, hard drive 407 and data repository 408 are operatively coupled to the CPU 404. The data repository 408 can include a memory and hard drive. In some situations, the data repository 408 is precluded. In some embodiments, the point of service system 400 includes a camera 409 (or in some cases a plurality of cameras, such as for three-dimensional imaging) for image and video capture. The point of service system 400 may include a sound recorder for capturing sound. Images and/or videos may be provided to a subject with the aid of the display 401. In other embodiments, the camera 409 may be a motion-sensing input device (e.g., Microsoft® Kinect®).

The camera 409 can be a two-dimensional camera or a three-dimensional camera. The camera 409 can capture still images and/or a video feed, in addition to sound. In some cases, the camera 409 is a thermal imaging camera, adapted to collect infrared radiation (IR) and correlate the collected light with the temperature of, for example, a user in view of the camera 409. In some cases, the camera 409 is a lens-less camera, such as a computation camera (e.g., Frankencamera).

The point of service system 400 is configured to implement questionnaire methods described herein. For instance, the point of service system 400 can implement the method 100 provided in FIG. 1. Questionnaire questions can be presented to a user remotely from the point of service system 400, such as with the aid of a network and user interface (e.g., GUI) of the remote device 403.

Figure 4B:
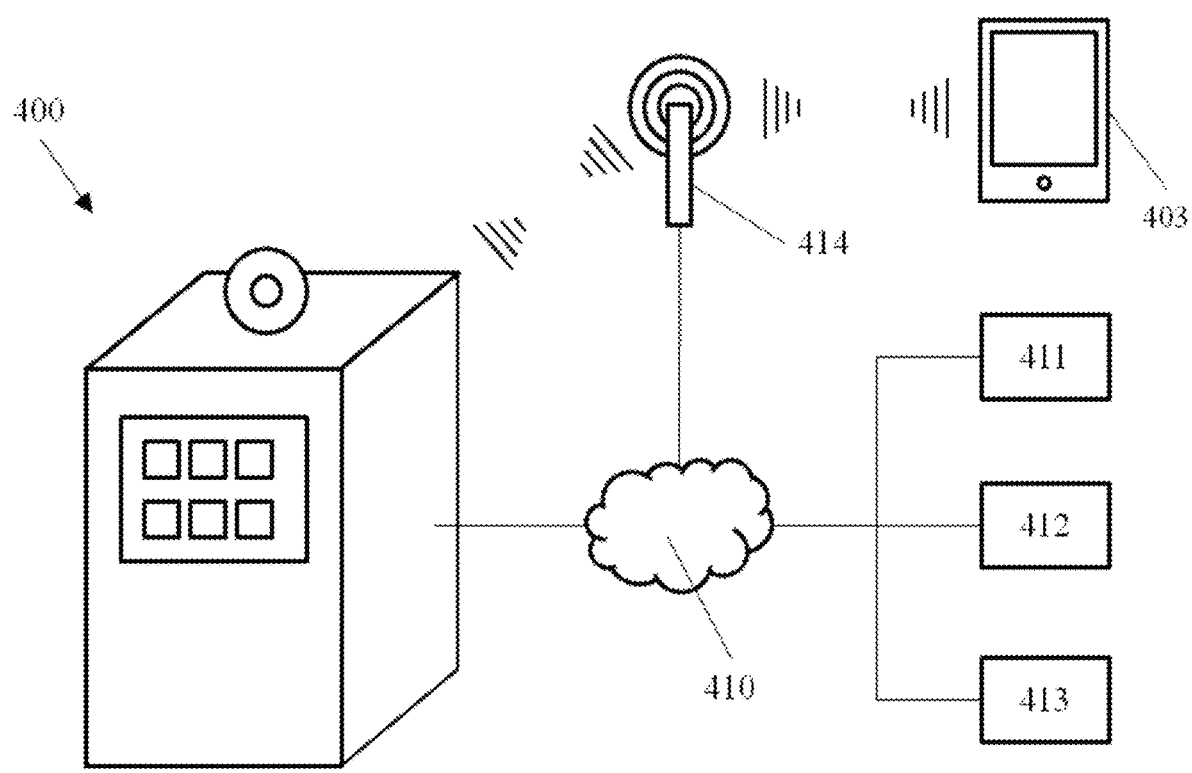

With reference to FIG. 4B, the point of service system 400 is configured to be in network communication with other devices through a network 410, which may be an intranet and/or the Internet. In the illustrated example, the point of service system 400 is in network communication with a first computer system 411, second computer system 412 and third computer system 413 that are located remotely from the point of service system 400. One or more of the computer systems 411, 412 and 413 may enable other users to access the point of service system 400 remotely. In some situations, one or more of the computer systems 411, 412 and 413 are data repositories for storing user information. In some cases, one or more of the computer systems 411, 412 and 413 are configured to enable data processing remotely from the point of service system 400.

The point of service system 400 can communicate with the network 410 and with the computer systems 411, 412 and 413 with the aid of the communications module 406 of the point of service system 400. The communications module 406 can include a wired or wireless interface for wired or wireless communication with the network 410, respectively.

In some cases, the point of service system 400 is configured to communicate with the network 410 through a wireless network access point 414. The wireless network access point 414 can be configured for communication using various wireless modes of communication, such as, for example, 2G, 3G, 4G, long term evolution (LTE), WiFi or Bluetooth. The communications module 406 of the system 400 can enable the system 400 to wirelessly communicate with the wireless network access point 414.

The remote device 403 can communicate with the point of service system 400 via a wireless interface of the point of service system 400, which may be included in the communications module 406. In an example, wireless communication can be via WiFi or Bluetooth connectivity. As shown in FIG. 4A, the remote device 403 communicates directly with the point of service system 400. In FIG. 4B, the remote device 403 communicates with the point of service system 400 via the wireless network access point 414. In an example, the remote device 403 communicates with the point of service system 400 through the wireless network access point 414 and subsequently the network 410. In another example, the remote device 403 communicates with the network 410 and subsequently with the wireless network access point 414 that is in wireless communication with the system 400 either directly or with the aid of another wireless network access point (not shown).

One or more sensors may be incorporated into the point of service system 400 and/or user interface 402. The sensors may be provided on the system housing, external to the system housing, or within the system housing. Any of the sensor types describing elsewhere herein may be incorporated. Some examples of sensors include optical sensors, sound, imaging, temperature sensors, motion sensors, depth sensors, pressure sensors, electrical characteristic sensors, gyroscopes or acceleration sensors (e.g., accelerometer), and pulse oximeter.

In an example, the point of service system 400 includes an accelerometer that detects, for example, when the point of service system 400 is being moved or when the point of service system 400 is not disposed on a preferable or ideal surface (e.g., horizontal surface), such as when the system has tipped over. In another example, the accelerometer detects when the system is being moved. In such circumstances, the point of service system 400 may shutdown to prevent damage to various components of the system 400. Prior to shutting down, the point of service system 400 may take a picture of a predetermined area on or around the system 400 with the aid of the camera 409.

The user interface 402 (e.g., graphical user interface) provides a questionnaire to a subject (or user). The questionnaire can include one or more questions. The questionnaire can be a guided questionnaire, including a series of questions of or related to a subject's dietary consumption, exercise, health condition and/or mental condition. In addition, the user interface 402 can display information relating to the operation of the point of service system 400 and/or data collected from the system 400. The user interface 402 may display information relating to a protocol that may be performed on the point of service system 400. The user interface 402 may include information relating to a protocol provided from a source external to the point of service system 400, or provided from the point of service system 400. The user interface 402 may display information relating to a subject and/or health care access for the subject. For example, the user interface 402 may display information relating to the subject identity and medical insurance for the subject. The user interface 402 may display information relating to scheduling and/or processing operation of the point of service system 400.

The user interface 402 may be capable of receiving one or more inputs from a user of the point of service system 400. For example, the user interface 402 is capable of receiving responses to questions provided to a subject as part of a questionnaire. In addition, the user interface 402 can receive instructions about one or more assay or procedure to be performed by the point of service system 400. The user interface 402 may receive instructions from a user about one or more sample processing steps to occur within the system 400. The user interface may receive instructions about one or more analytes to be observed.

The user interface 402 is capable of receiving information relating to the identity of a subject. The subject identity information may be entered by the subject or another operator of the device or imaged or otherwise captured by the user interface 402 itself. Such identification may include biometric information, issued identification cards, or other uniquely identifiable physiological (e.g., biological) or identifying features, materials, or data. The user interface 402 may include one or more sensors that assist with receiving identifying information about the subject. The user interface 402 may have one or more questions or instructions pertaining to the subject's identity to which the subject may respond. In some cases, the user interface 402 may request a password and/or security question(s) from the subject.

In some embodiments, the user interface 402 is configured to display a questionnaire to a subject. The questionnaire can include questions about the subject's dietary consumption, exercise, health condition and/or mental condition. The questionnaire can be a guided questionnaire having one or a plurality of questions presented to the subject through one or more screens, as displayed on the display 401 or a display of a remote device, such as the remote device 403. The plurality of questions may be presented to the subject sequentially (i.e., one after another). The questionnaire may be presented to the subject with the aid of one or a combination of text, images, video or sound. In some situations, the user interface 402 is a graphical user interface and the questionnaire is presented to the subject on the display 401 with the aid of one or more of textual, graphical, audio and video elements.

In some cases, the remote device 403 comprises a camera that is configured retrieve visual and/or auditory information relating to the dietary consumption, exercise, health condition and/or mental condition of a user. Such visual and/or auditory information (e.g., image, video, sound) can be used to respond to questionnaire questions, or to collect information to enable the system 400 to monitor the dietary consumption, exercise, health condition and/or mental condition of the user. In an example, the camera of the remote device (e.g., iPhone®) can be used to capture an image of a food item. The image can be subsequently directed to the system 400 or directed to a remote system, such as the cloud. The system 400 can subsequently use the image as a response to a questionnaire question (e.g., if the user was asked by the system 400 to take a picture of a "large" apple). Alternatively, the system 400 can analyze such information collected by the remote device 403 to determine portion size of the dietary consumption, exertion level of the exercise, existing state of health condition and/or existing state of mental condition. In an example, the system 400 can analyze an image of a food item captured by a camera of the remote device 403 to estimate the portion size of the food item and, in some cases, the caloric information of the food item.

The system 400 can use information collected by a user, such as with the aid of the remote device 403, to supplement the user's responses to questionnaire questions, or in some cases to test the user's responses for accuracy. The system 400 can use such user input to update or otherwise refine a calibration matrix of the user. In some cases, such user input includes photographs (or pictures) of items that related to the user's dietary consumption, exercise, health condition and/or mental condition. Such user input can be provided with reference data, such as a reference image of an item having known dimensions (e.g., diameter, thickness). In some cases, the reference data and user input can be provided in the same frame.

For example, the system 400 can request that the user take a picture of a "large apple" and the user can take a picture of what the user find to be a large apple. The system 400 can request that the user take a reference picture of an item for which the system 400 has readily identifiable dimensions, such as the picture of a coin (e.g., United States Quarter). The reference picture can be used to determine a size of the picture of the apple. The reference picture can be provided in the same frame as the picture of the apple. The system 400 can then compare the picture of the "large apple" taken by the user with responses to calibration questions directed at apple sizes to determine whether the system's calibration is acceptable or unacceptable. In the latter case, the system can update the system's calibration as to apple sizes in view of the user's response. For example, the system 400 can digitize the picture of the apple taken by the user, assign the picture a numerical value that is indicative of the size of the apple in the picture, correlate the size with how the user perceives the apple (e.g., "large apple"), and input the numerical value in a calibration matrix (see, e.g., FIG. 3) of the system under "large apple."

A user interface, such as a graphical user interface (GUI), can be implemented on the display 401 of the system 400, or on a display of the remote device 403, or a display of the first computer system 411, second computer system 412 and/or third computer system 413.

Textual, graphical, audio and video elements can be presented to a subject with the aid of hardware and/or software configured to generate and display (or provide) the textual, graphical, audio and video elements. The software can include, for instance, a web browser implementing (e.g., compiling) machine executable instructions in the form of machine-readable code, such as hypertext markup language (e.g., HTML 5), JavaScript, C sharp, Java/J++, C++(or other object-oriented code). In some situations, such software is rendered with the aid of a Web browser, Adobe® Flash®, or the like. Graphical elements can include images, widgets and icons that aid in implementing the questionnaire.

The user interface 402 may be capable of receiving additional information relating to the subject's dietary consumption, exercise, health condition and/or mental condition. The additional information may be entered directly by the subject or another operator of the system 400. The subject may be prompted by one or more questions or instructions from the user interface and may enter information in response. The questions or instructions can relate to qualitative aspects of the subject's life (e.g., how the subject is feeling). In some embodiments, the information provided by the subject is qualitative and not quantitative. In some instances, however, the subject may also provide quantitative information, such as, for example, the subject's weight. In some cases, information provided by the subject may pertain to one or more analyte levels within a sample from the subject.

In some embodiments, the system 400 is configured to communicate with one or more peripheral devices configured to collect information as to the subject's dietary consumption, exercise, health condition and/or mental condition. The one or more peripheral devices can be selected from a weight scale, blood pressure monitor, glucose monitor, hear rate monitor, electronic device with a camera, pulse oximeter, and/or other local analytical system. The electronic device with the camera may include image recognition software; alternatively, the system 400 or remote server can include image recognition software to enable the system 400 to recognize the subject's food from a picture taken by the electronic device.

In some cases, during questionnaire (or survey) the point of service system 400 can also collect information relating to therapy and/or medications undergone or currently taken by the subject. The user interface 402 may prompt the subject using a survey or similar technique. In such a case, the questionnaire can include graphics, images, video, audio, and/or other media.

The questionnaire may have a fixed set of questions and/or instructions, or, alternatively, questions that are not fixed and which can vary based on the user's responses. In some cases the questionnaire can provide the user with a fixed set of questions, while in other cases the questions can vary. In an example, the point of service system 400 has a machine learning algorithm that learns from a subject's responses to questions, including reference questions, and provides additional questions based on the subject's responses. In some cases the questions vary based on the information gleaned from the system 400 in response to the user's previous questions. The survey (e.g., the sequence and/or content of the questions) may dynamically change depending on the subject's answers. In an example, if the system 400 determines that the subject is being inconsistent as to the subject's responses to reference questions, the system 400 can ask follow-up questions.

Identifying information about the subject and/or additional information relating to the subject can be stored in the system 400 and/or transmitted to an external device or cloud computing infrastructure through the network 410, for example. Such information may be useful in analyzing data relating to a sample collected from the subject, or for monitoring a subject's health or well-being. Such information may also be used by insurance providers to make decisions as to the subject's insurance coverage (e.g., premiums).

The user interface 402 and/or sensors of the system 400 may be capable of collecting information relating to the subject or an environment of or relating to the subject. For example, the system 400 may collect information through a screen, thermal sensor, optical sensor, imaging device, motion sensor, depth sensor, pressure sensor, electrical characteristic sensor, acceleration sensor (e.g., accelerometer), any/or other type of sensor described herein or known in the art. In an example, the optical sensor may be or be part of a camera (such as, e.g., the camera 409). The optical sensor may capture one or more static images of the subject and/or video images of the subject.

With the aid of the camera 409 the system 400 may collect an image of the subject. The image may be a 2D image of the subject. The system 400 may collect a plurality of images of the subject that may be used to determine a 3D representation of the subject. The system 400 may collect a one-time image of the subject. The system 400 may collect images of the subject over time. The system 400 may collect images with any frequency. In some embodiments, the system 400 may continually collect images in real-time. The system 400 may collect a video of the subject. The system 400 may collect images relating to any portion of the subject, including, but not limited to, the subject's eye or retina, the subject's face, the subject's neck, the subject's hand, the subject's fingertip, the subject's torso, and/or the subject's overall body. The images collected of the subject may be useful for identifying the subject and/or for diagnosis, treatment, monitoring, or prevention of a disease for the subject. In some instances, images may be useful for determining the subject's height, circumference, weight, or body mass index. The system 400 may also capture the image of a subject's identification card, insurance card, or any other object associated with the subject.

In some situations, the camera 409 can be used to enable a user to communicate with another user, such as a healthcare provider. The system 400 can permit the user to communication with another user in a synchronous fashion such that the communication is live, or in an asynchronous fashion. Under asynchronous communication, the system 400 collects a sound, image and/or video of the user and transmits the collection sound, image and/or video to a remote system of another user who can then review collected sound, image and/or video at a later point in time.

The point of service system 400 may also collect audio information from the subject. Such audio information may include the subject's voice or the sound of one or more biological processes of the subject. For example, the audio information can include the sound of the subject's heartbeat or a sound associated with the subject breathing.

The point of service system 400 may collect biometric information about a subject. For example, the point of service system 400 can collect information about the subject's body temperature. In another example, the point of service system 400 can collect information about the subject's pulse rate. In some instances, the point of service system 400 can scan at least a portion of a tissue or body part of the subject, such as the subject's retina, fingerprint or handprint. In some cases, the point of service system 400 may determine the subject's weight. The point of service system 400 may also collect a sample from the subject and sequence the subject's genes (e.g., DNA) or a portion thereof. The point of service system 400 may also collect a sample from the subject and conduct a proteomic analysis thereon. Such information may be used in the operation of the system 400. Such information may relate to the diagnosis or the identity of the subject. In some embodiments, the point of service system 400 may collect information about the operator of the system who may or may not be different from the subject. Such information can be useful for verifying the identity of the operator of the system.

In some instances, such information collected by the point of service system 400 can be used to identify the subject. The subject's identity may be verified for insurance or treatment purposes. The subject identify may be tied to the subject's medical records. In some instances, the data collected by the point of service system 400 from the subject and/or sample may be linked to the subject's records. The subject identity may also be tied into the subject's health insurance (or other payer) records. Compliance with drug dosing regimes can be ascertained by the frequency with which the medication is renewed, as communicated from pharmacy databases.

In some instances, such information, including medical records, can be augmented with the subject's responses to questionnaire questions. This can permit a healthcare provider to correlate the subject's health and/or mental condition with the subject's responses to questionnaire questions that relate to the subject's dietary consumption, exercise, health condition and/or mental condition.

Responses to questionnaire questions can be used to determine a subject's eligibility. In an example, an individual arrives at a point of service location and performs an eligibility test to see if the individual is eligible for one or more tests. The individual may then be pre-screened and can answer one or more questions provided by a questionnaire. The questionnaire can include reference questions, as described elsewhere herein. The questionnaire can include questions about the subject's lifestyle (e.g., diet, exercise, habits) and/or medical history. A physician can perform a physician check of the individual. In some situations, the questionnaire includes questions about the subject's dietary consumption, exercise, health condition and/or mental condition. The subject's health condition may be related to the subject's physiological condition. The subject's mental condition may be related to the subject's mood or other mental condition, such as depression. The questionnaire may be a guided questionnaire, having a plurality of questions of or related to the subject's dietary consumption, exercise, health condition and/or mental condition that are presented to a user in a predetermined order. In some situations, the questionnaire is presented to the subject with the aid of a system (or sub-system) of the point of service system 400 configured to learn from the subject's responses and tailor subsequent questions in response to the subject's responses. In some cases, questionnaire results can also be used to prepare the SPU for any expected complications in sample processing and/or chemical assays. In an example, a subject identifying him or herself as a smoker can trigger a flag for expected high hematocrit, thereby requiring careful extraction of plasma from the centrifuged sample.

In some embodiments, lifestyle recommendations may be made to the subject by the point of service system 400 and/or a system associated with the point of service system 400. Such recommendations may be provided prior to, concurrently with, or subsequent to the subject completing the questionnaire. Such recommendations may be made based on the information gathered within the questionnaire, medical records, biochemical data, and/or test results. For example, the system could provide information to a subject about how the subject's perception of a level or amount relating to dietary consumption, exercise, health condition and/or mental condition relates to a quantifiable standard. In some embodiments, a point of service system 400 and/or a system associated with the point of service system 400 may help educate a subject regarding his or her health or other condition.

In some embodiments, the point of service system 400 interprets subject responses to questions with the aid of reference information comprising a pictorial depiction of portion size of the dietary consumption, exertion level of the exercise, existing state of health condition and/or existing state of mental condition. The reference information may be included in a calibration matrix stored in a memory location (e.g., cache, hard drive, flash memory) of the system 400. Alternatively, subject responses can be interpreted with the aid of a server located remotely from the point of service system 400. The server can include a calibration matrix.

In some situations, the point of service system 400 and/or health care personnel can collect biometric information about the subject being monitored, such as, e.g., blood pressure, weight, body temperature. This may be coupled with a test of a sample collected from the subject, which may be processed by the point of service system 400. All of the information may be linked and may be accessible by the clinical decision support system. In some embodiments, all the information may be linked within a single subject's records. Such procedures may be useful for annual checkups or preventative care. Such procedures may also be useful for diagnosing, treating, and/or monitoring a disease.

In some embodiments, the point of service system 400 is operatively coupled to one or more sensors for making qualitative or quantitative measurements of a subject. Such measurements may relate to the subject's dietary consumption, exercise, health condition and/or mental condition. The one or more sensors can be selected from weight sensors, eye sensors, body temperature sensors, blood pressure sensors, heart rate sensors, brain wave sensors, humidity sensors and pH sensors. In an example, a subject's weight scale is configured to communicate with the point of service system 400 during or subsequent to the subject taking a measurement of the subject's weight. The point of service system 400 can collect the subject's weight and store that in a memory location, in some cases with a timestamp associated with the point at which the subject's weight was measured. Alternatively, the weight scale can transmit information relating to the subject's weight to the remote device 403, which can subsequently transmit the information to the system 400.

Information as to a user's dietary consumption, exercise, health condition and/or mental condition can be maintained in a user profile. In some cases, the profile can be maintained in a memory location of a device or system implementing the methods provided herein, such as, for example, the system 400 of FIGS. 4A and 4B. In other cases, the profile can be maintained in a memory location of a computer system remote from the device of system implementing the method provided herein. In some situations, the profile can be accessed by the user and edited, updated or deleted.

In some situations, details as to a user's dietary consumption, exercise, health condition and/or mental condition can be provided by a device associated with the user. For instance, the distance a user has walked, which may be relevant to an activity of the user, can be provided by a device having an accelerometer or pedometer and software for recording distance traveled. Such a device can be in communication with a device for keeping a record of the user's dietary consumption, exercise, health condition and/or mental condition, such as the system 400. Such a system can be in communication with a system for collecting such information and for updating a user's profile. For instance, the information can be uploaded to the system 400 and used to update the user's activity diary.

As an example, the intensity of the user's activity can be measured using an accelerometer, which can be included in a portable electronic device (e.g., iPhone). The intensity information can be transferred to a device or system keeping a record of the user's dietary consumption, exercise, health condition and/or mental condition, such as the system 400, and further calibrated with the aid of reference information. In some situations, the intensity information can be calibrated on the portable electronic device using the methods described above.

In some cases, the system 400 includes various sub-systems to collect physiological data from a user (or subject). Examples of sub-systems include, without limitation, a blood pressure cuff, pulse oximeter, temperature sensor (e.g., thermometer), lie detector, and iris scanner for measuring iris dilation. The sub-systems can be included in the system 400, or coupled to the device as peripheral devices.

The system (or device) 400 can be as described in U.S. patent application Ser. No. 13/244,946 to Holmes ("SYSTEMS AND METHODS FOR COLLECTING AND TRANSMITTING ASSAY RESULTS") and U.S. patent application Ser. No. 13/244,947 to Holmes et al. ("SYSTEMS AND METHODS FOR MULTI-ANALYSIS"), which applications are entirely incorporated herein by reference. For instance, the system 400 can include a plurality of modules mounted on a support structure. An individual module of the plurality of modules can comprise a sample preparation station, assay station, and/or detection station. In addition, the system 400 can be configured to perform (a) at least one sample preparation procedure selected from the group consisting of sample processing, centrifugation, separation, and chemical processing, and (b) multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof. The multiple types of assays are performed with the aid of isolated assay units contained within the system 400.

In some situations, the system 400 can access a network with the aid of systems and methods disclosed in U.S. patent application Ser. No. 13/244,836 to Balwani ("NETWORK CONNECTIVITY SYSTEMS AND METHODS"), which application is entirely incorporated herein by reference.

Figure 5:
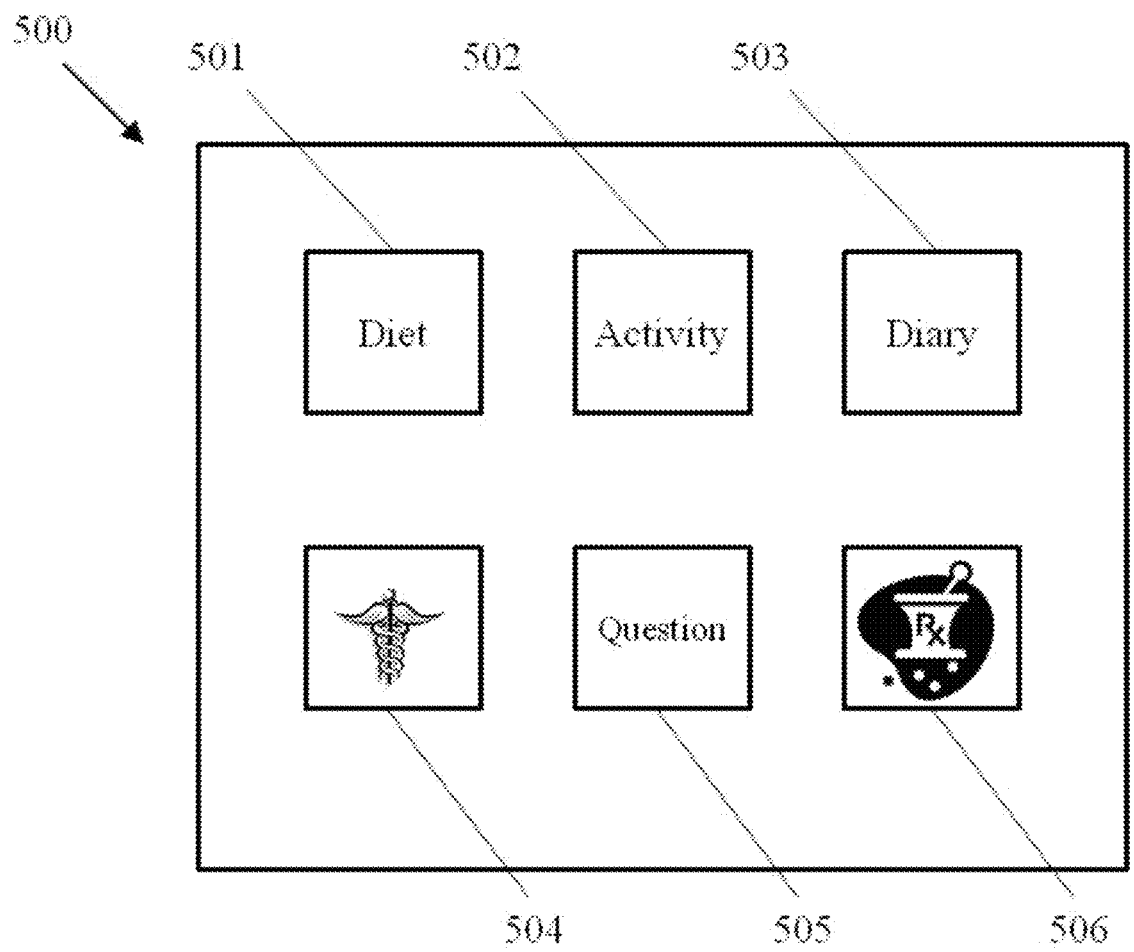
FIG. 5 shows an illustrative example of a graphical user interface.

Information can be exchanged to and from a user with the aid of a graphical user interface implemented on a system or device provided herein. In some embodiments, a graphical user interface includes a plurality of icons or buttons. FIG. 5 shows an exemplary graphical user interface (GUI) 500, as can be implemented on the point of service system 400 or a remote computer system, such as the remote device 403. The GUI 500 includes a diet module 501, activity module 502, diary module 503, physiological data module 504, question module 505, and prescription database module 506. Each module can be implemented using an application (or "app") configured to be executed or otherwise implemented on an operating system of a device hosting the GUI 500.

Each of the modules 501-506 can aid in collecting information from a subject by presenting a subject with a series of questions, such as with the aid of a guided questionnaire (or survey), as described herein. The diet module 501 can be used to collect dietary information from a subject. Dietary information can include details as to the material (edible or inedible) the subject has consumed (e.g., liquid, solid, or semi-solid material) or is contemplating eating or drinking. The activity module 502 can be used to collect information as to the subject's one or more activities, such as exercise routines and sports. The diary module 503 can be used to collect information as to a subject's daily routines, such as the subject past activities, current activities or future activities, in addition to the subject's thoughts and recollections. The physiological data module 504 can be used to collect information relating to a subject's physiological data, such as, for example, temperature, heart rate, oxygen saturation, and/or skin conductivity. The question module 505 is used to enable a subject to ask the system or a healthcare provider a question, such as a question relating to the subject's health. The prescription database module 506 is used to assist the subject in fulfilling a prescription, such as by ordering one or more drugs at a pharmacy, which may be in communication (e.g., network communication) with a device having the modules 501-506.

The question module 505 can enable a user to initiate a conversation with a system, such as to ask the system questions (e.g., health related questions). In an example, the system 400 is provided at a pharmacy or other professional location (e.g., doctor's office waiting room, hospital lobby) and the system 400 provides the user questions and answers to determine whether a drug regimen or treatment of the user may require modification, and if so, recommend to that user that the user should consult a doctor or healthcare provider for further information on the user's drug regimen.

The modules 501-506 can be implemented on a point of service device, such as the point of service system 400, or a remote computer system, such as the remote device 403. Each module can be linked to a questionnaire (or survey) having one or more questions and, in some cases, one or more reference (or calibration) questions, as described herein.

In another embodiment, provided herein is a computer readable medium comprising machine-executable code implementing a method for calibrating user responses to questions relating to dietary consumption, exercise, health condition, or mental condition. The method can be any method described herein. In some embodiments, the method comprises presenting, with the aid of a computer system and an interactive display operatively coupled to the computer system, a query to a user, the query relating to the user's dietary consumption, exercise, health condition and/or mental condition. Next, with the aid of the computer system having a computer processor (also "processor" herein) and interactive display, a response to the query from the user is received. With the aid of the computer system, the response is interpreted based on a set of reference information. The set of reference information comprises a pictorial depiction of portion size of the dietary consumption, exertion level of the exercise, existing state of health condition, and/or existing state of mental condition.

A questionnaire can be implemented on a system having a processor and a memory location having machine-executable code implementing a method. Aspects of devices, systems and methods provided herein can be embodied in programming. Various aspects of the technology may be thought of as "products" or "articles of manufacture" typically in the form of executable code and/or associated data that is carried on or embodied in a type of machine readable medium. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server or an intensity transform system. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Example 1

Figure 6:
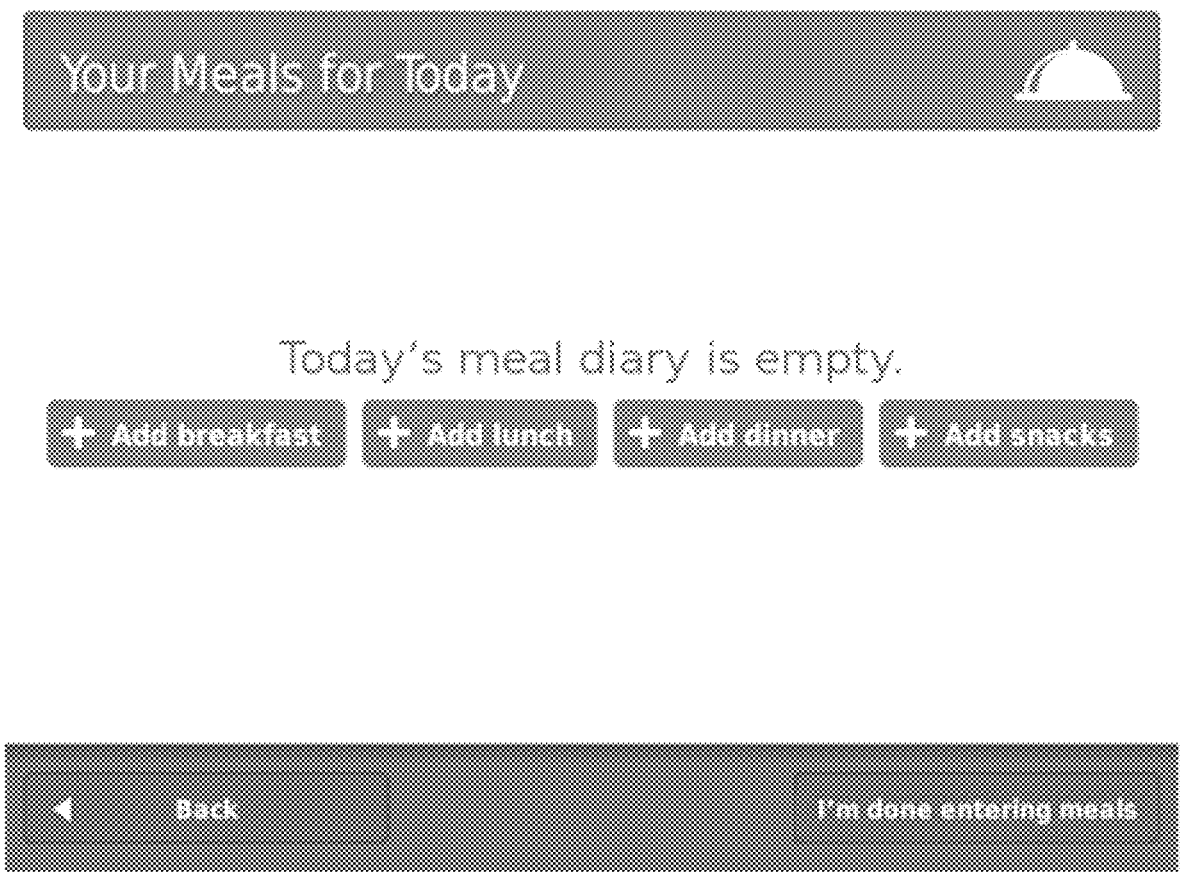
FIG. 6 shows an illustrative example of a screenshot of a graphical user interface having a survey for collecting information as to a user's dietary consumption.

FIG. 6 is a screenshot of a graphical user interface (GUI) having a survey for collecting information as to a user's dietary consumption. The information can be collected from the user. The GUI can be implemented by a system having an interactive display, such as the system 400 of FIGS. 4A and 4B. The GUI can permit a user to input various breakfast, lunch, dinner and snack items. For instance, the user can input a breakfast item by pressing "+Add breakfast." The GUI shows an empty "meal diary," which the user can populate by pressing any of "+Add breakfast," "+Add lunch," "+Add dinner," and "+Add snacks."

For instance, the user can select "+Add lunch" to provide details as to what the user consumed for lunch. The system then asks the user to indicate what the user consumed for lunch (e.g., with the aid of a text input box or drop-down menu with options). The system then asks the user to indicate the quantity consumed.

Figure 7:
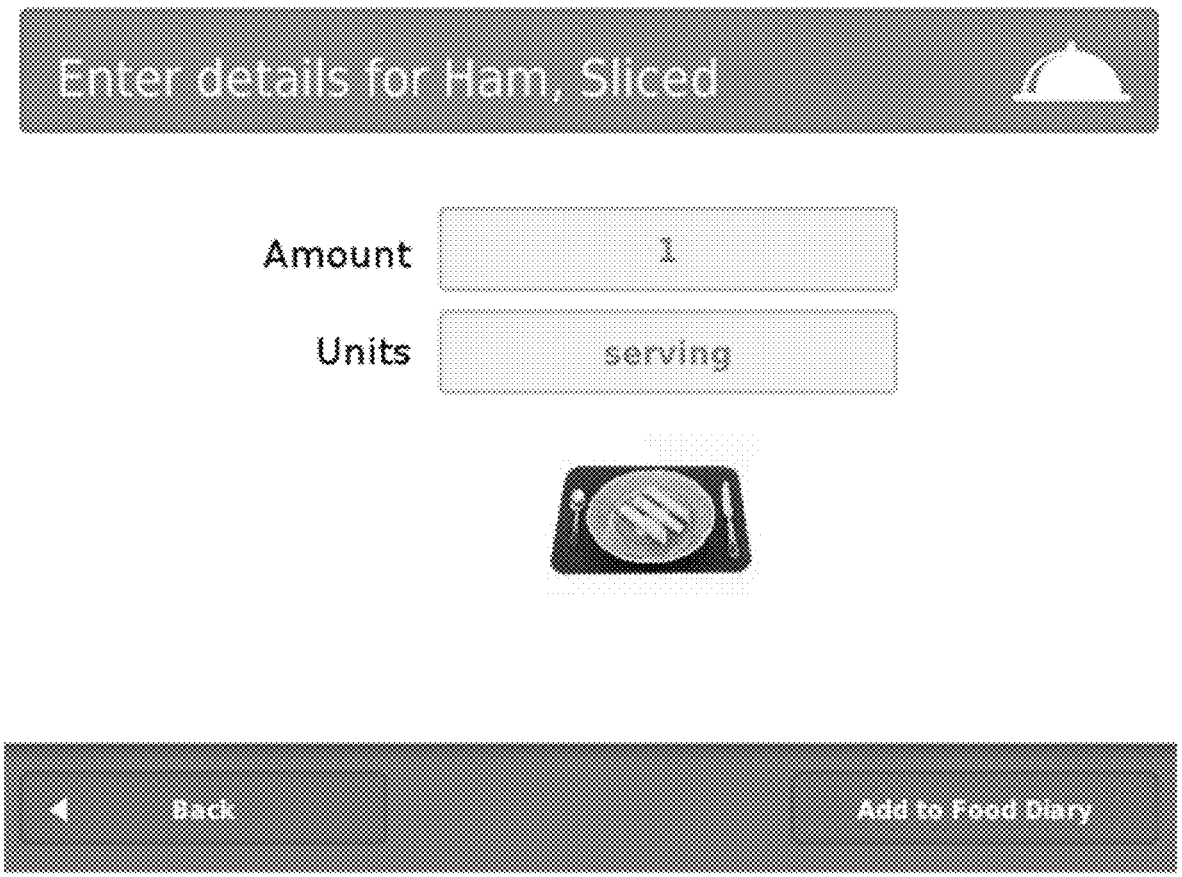
FIG. 7 shows an illustrative example of a screenshot of a graphical user interface in which the user selects "Ham, Sliced"

With reference to FIG. 7, in an example, the user selects "Ham, Sliced" for lunch. The system then asks the user for the "Amount" and "Units" of ham consumed. The user provides "1" and "Serving" as inputs for the amount and units, respectively. The system then asks the user a calibration (or reference) question to interpret what the user means by a single serving. With reference to FIG. 8, in a new screen, the system asks the user "How big is 1 serving of sliced ham?" The system provides the user three options ("Picture 1," "Picture 2," and "Picture 3") of different sizes to choose from. The user selects the picture that best approximates a single serving of sliced ham.

The system presents the user with various GUI menu items to enable the user to add food, remove food, or edit a response. The user may add other foods to the user's food diary by pressing "Add Food to Diary" GUI menu item. The user can modify or edit responses to any of the questions by pressing the "Back" GUI menu item.

Example 2

Figure 9:
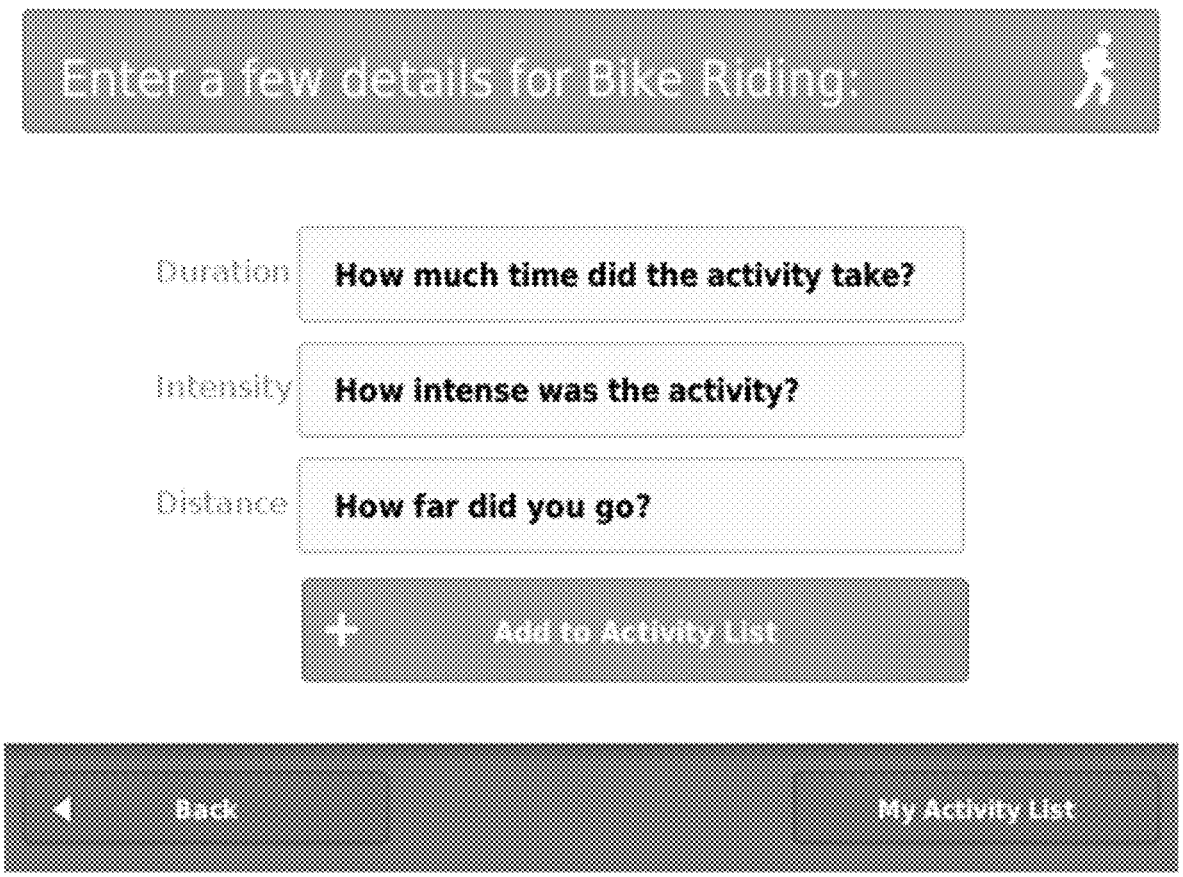
FIG. 9 shows an illustrative example of a screenshot of a graphical user interface having a survey for collecting information on a user's bike riding activity.

FIG. 9 is a screenshot of a graphical user interface (GUI) having a survey for collecting information on a user's bike riding activity. The information can be collected from the user. The GUI can be implemented by a system having an interactive display, such as the system 400 of FIGS. 4A and 4B. In the illustrated example, the user selects "Bike Riding" from various activity options and the system asks the user to input "Duration," "Intensity," and "Distance." The GUI provides the user questions to assist the user in inputting the requested information, such as "How much time did the activity take?" The user can provide the information in the boxes with the questions.

The GUI provides the user various GUI menu items, such as navigating to a previous screen ("Back") and viewing an activity list of the user ("My Activity List"). The GUI also provides the user the option to input other activities by pressing "+Add to Activity List."

Figure 10:
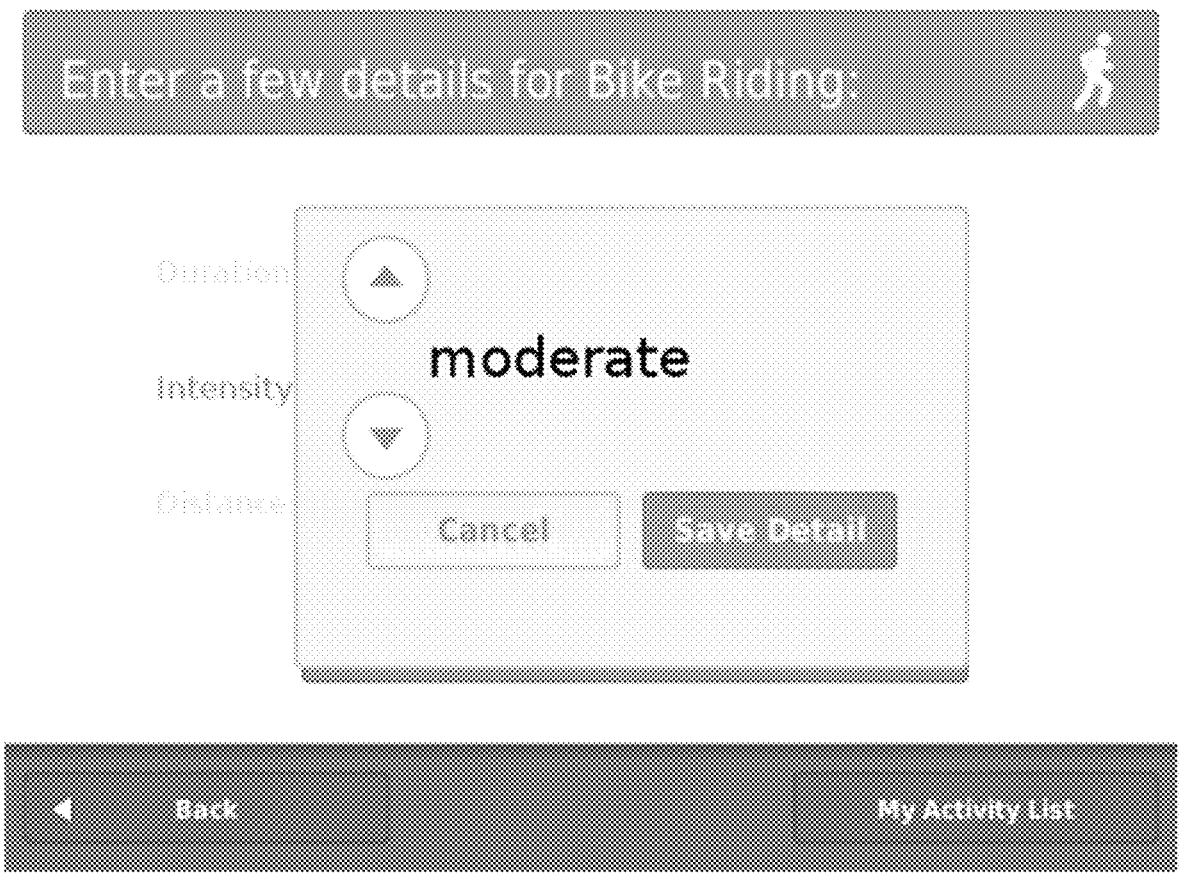
FIG. 10 shows an illustrative example of a screenshot showing the intensity "moderate"

In FIG. 10, the user selects the "Intensity" field and chooses from various options to characterize the intensity of the user's bike riding activity. The user selects "moderate" as the intensity and selects "Save Detail" to proceed to the next step.

Figure 11:
FIG. 11 shows an illustrative example of a screenshot of a reference question for interpreting the information provided by the user in FIG. 10.
Figure 11:
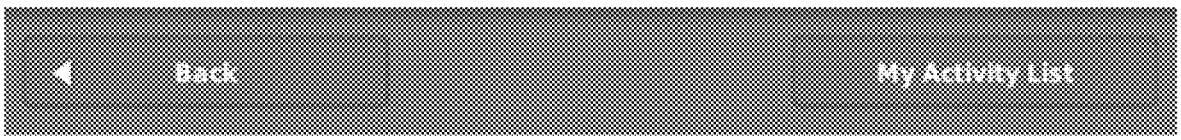

With reference to FIG. 11, the system asks the user a reference question to interpret what the user means by "moderate." The system provides the user three picture options ("Picture 1," "Picture 2," and "Picture 3") to choose from, at least one of which may approximate moderate intensity. For instance, "Picture 1" may show a user walking, "Picture 2" may show a user jogging, and "Picture 3" may show a user sprinting. The user selects the picture that best approximates moderate intensity for the user.

Example 3

Figure 12:
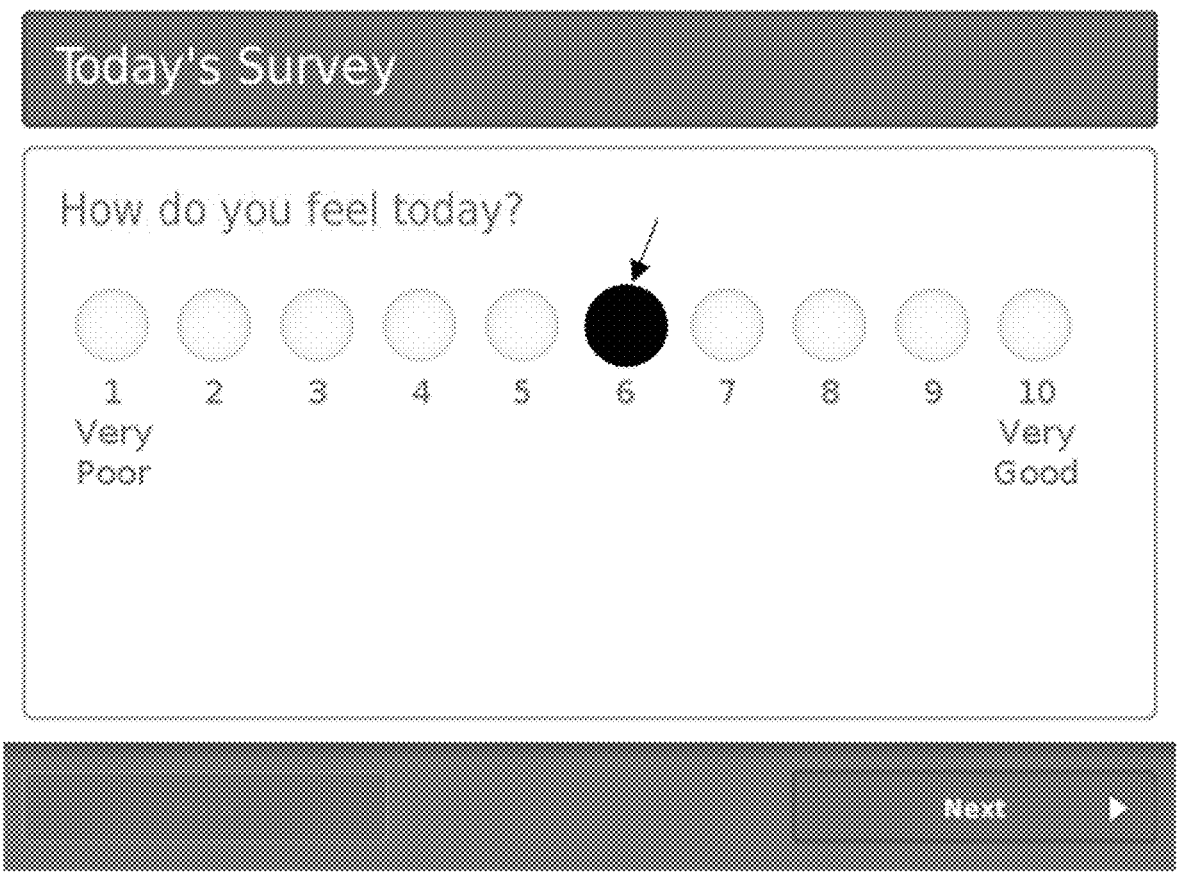
FIG. 12 shows an illustrative example of a screenshot of a graphical user interface having a survey for collecting information on a user's condition.

FIG. 12 is a screenshot of a graphical user interface (GUI) having a survey for collecting information on a user's mental condition, such as mood. The GUI can be implemented by a system having an interactive display, such as the system 400 of FIGS. 4A and 4B. In the illustrated example, the system has asked the user to select an integer from 1 to 10 that captures the user's mood, with 1 corresponding to "Very Poor" and 10 corresponding to "Very Good." The user selects 6. The system then permits the user to proceed along the survey by pressing "Next." With reference to FIG. 13, the system then asks the user a reference question to interpret what the user means by well-being 6, as selected by the user in FIG. 12. The system provides the user three picture options ("Picture 1," "Picture 2," and "Picture 3") to choose from, at least one of which may approximate well-being 6. For instance, "Picture 1" may show an individual with a sad facial expression, "Picture 2" may show an individual with a neutral facial expression, and "Picture 3" may show an individual with a smile. The user selects the picture that best approximates well-being number 6.

In some cases, the picture options change based on the user's response to questionnaire questions and/or calibration questions. For instance, the three picture options presented to the user for well-being 1 can be different from the three picture options presented to the user for well-being 6.

While the above is a complete description of the preferred embodiments of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Also, as used in the description herein and throughout the claims follow, terms of "include" and "contain" are open ended and do not exclude additional, unrecited elements or method steps. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A method for calibrating user responses to questions comprising:
   (a) presenting on a bodily sample processing device, with the aid of a computer system and an interactive display operatively coupled to the computer system, a query to a user, said query relating to said user's health condition or mental condition wherein the sample processing device comprises a pipette, a centrifuge, and a cytometer;
   (b) receiving, with the aid of said computer system and interactive display, a response to said query from said user;
   (c) interpreting, with the aid of a computer processor, said response based on a set of reference information, wherein said set of reference information comprises a pictorial depiction of existing state of said health condition or existing state of said mental condition;
   (d) obtaining a bodily fluid sample from the user; and
   (e) changing the processing of the sample in the bodily sample processing device based on the user's response;
   wherein said presenting comprises displaying a customizable menu screen containing a choice of at least one of the following applications:
      a health condition component having information concerning said user's health, and an interface for responding to queries or entering information related to said user's health condition;
      a mental condition component having information concerning said user's mental condition, and an interface for responding to queries or entering information related to said user's mental condition; and
      a calibration questionnaire component, wherein said user is presented with at least one choice of pictorial elements relating to health condition or mental condition, and said user's choice of a pictorial element is used to build a calibration matrix to interpret said user's perception of existing state of said health condition or existing state of said mental condition.

2. The method of claim 1, further comprising, subsequent to step (c), monitoring the health of said user.

3. The method of claim 1, wherein said reference information is obtained by providing to said user a choice of at least two pictorial elements, wherein said pictorial elements depict the existing state of said health condition, or the existing state of said mental condition.

4. The method of claim 1, wherein said reference information is utilized to yield a calibration matrix to calibrate said user's response to said query.

5. The method of claim 1, wherein said interactive display is a capacitive touch or resistive touch display.

6. The method of claim 1, wherein said reference information is obtained prior to said query.

7. The method of claim 1, wherein said reference information is obtained subsequent to said query.

8. The method of claim 1, wherein said response is interpreted with the aid of a calibration matrix residing on a memory location of said computer system.

9. The method of claim 1, wherein said query is presented to said user with the aid of a graphical user interface (GUI) on said interactive display.

10. The method of claim 9, wherein said GUI comprises a customizable menu screen containing a choice of at least one of the following applications:
    (a) a dietary consumption component, including information concerning said user's diet and an interface for entering food, drink or other related information; and
    (b) an exertion level component having information related to said user's activity habits or schedule, and an interface for entering user-specific activity information, exercise or other user-specific activity-related information.

11. A system for calibrating user responses to questions comprising:
    a bodily sample processing device comprises a pipette, a centrifuge, and a cytometer;
    an interactive display configured to present machine-generated graphical items to a user; and
    a computer system operatively coupled to said interactive display, said computer system having a memory location comprising machine-executable code implementing, with the aid of a processor of said computer system, a method comprising:
    (a) presenting, with the aid of said computer system and interactive display, a query to a user, said query relating to said user's health condition or mental condition;
    (b) receiving, with the aid of said computer system and interactive display, a response to said query from said user; and
    (c) interpreting, with the aid of said computer system, said response based on a set of reference information, wherein said set of reference information comprises a pictorial depiction of existing state of said health condition, or existing state of said mental condition;
    (d) obtaining a bodily fluid sample from the user; and
    (e) changing the processing of the sample in the bodily sample processing device based on the user's response.

12. The system of claim 11, wherein said reference information is utilized to yield a calibration matrix to calibrate said user's response to said query.

13. The system of claim 11, wherein said interactive display is a capacitive touch or resistive touch display.

14. The system of claim 11, wherein said response is interpreted with the aid of a calibration matrix residing on a memory location of said computer system.

15. The system of claim 11, wherein said memory location comprises machine executable code for implementing, on said interactive display, a graphical user interface (GUI).

16. The system of claim 15, wherein said GUI comprises a customizable menu screen containing a choice of at least one of the following applications:

(a) a dietary consumption component, including information concerning said user's diet and an interface for entering food, drink or other related information; and
(b) an exertion level component having information related to said user's activity habits or schedule, and an interface for entering user-specific activity information, exercise or other user-specific activity-related information.

17. The system of claim 16, wherein one or more responses to said at least one of the following applications are interpreted using an internal calibration matrix of said user's perception of portion size of said dietary consumption, exertion level of said exercise, existing state of health condition or existing state of mental condition.

18. The system of claim 17, wherein said internal calibration matrix is stored on a memory location of said computer system.

19. The system of claim 16, wherein said customizable menu screen contains a choice of at least two of said applications.

20. A method for calibrating user responses to questions relating to dietary consumption, exercise, health condition, or mental condition, comprising:
(a) presenting on a point-of-service bodily fluid sample processing device, with the aid of a computer system and an interactive display operatively coupled to the computer system, a query to a user, said query relating to said user's dietary consumption, exercise, health condition and/or mental condition;
(b) receiving, with the aid of said computer system and interactive display, a response to said query from said user; and
(c) interpreting, with the aid of a computer processor, said response based on a set of reference information, wherein said set of reference information comprises pictorial depictions displayed to the user showing existing state of health condition and/or existing state of mental condition, wherein the set of reference information is generated by i) the user selecting pictorial depictions that best matches their qualitative descriptions and ii) mapping quantitative information associated user selected pictorial depictions to quantify user qualitative descriptions;
(d) obtaining a bodily fluid sample from the user;
(e) changing the processing of the sample in the bodily fluid sample processing device based on the user's response; and
(f) using the bodily fluid sample processing device to process the bodily fluid sample, wherein the sample processing device comprises a pipette, a centrifuge, and a cytometer.

* * * * *